United States Patent
Steiner et al.

(10) Patent No.: US 6,706,043 B2
(45) Date of Patent: Mar. 16, 2004

(54) SELF-CUTTING, HOLLOW-CYLINDRICAL BONE ANCHORING ASSEMBLY

(75) Inventors: Beatrice Steiner, Cham (CH); Max Aebi, Québec (CA)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/788,616

(22) Filed: Feb. 21, 2001

(65) Prior Publication Data

US 2001/0007072 A1 Jul. 5, 2001

Related U.S. Application Data

(63) Continuation of application No. PCT/CH98/00359, filed on Aug. 21, 1998.

(51) Int. Cl.⁷ ............................................. A61B 17/68
(52) U.S. Cl. ......................................... 606/60; 606/72
(58) Field of Search ........................ 606/57, 60, 61, 606/72, 73, 79; 411/413, 386, 387.1, 387.5, 395

(56) References Cited

U.S. PATENT DOCUMENTS

| | | | | |
|---|---|---|---|---|
| 2,532,296 A | * | 12/1950 | Giesen | 606/73 |
| 4,484,570 A | * | 11/1984 | Sutter et al. | 606/72 |
| 4,537,185 A | | 8/1985 | Stednitz | 128/92 |
| 4,632,100 A | * | 12/1986 | Somers et al. | 606/73 |
| 5,015,247 A | | 5/1991 | Michelson | 606/61 |
| 5,098,435 A | * | 3/1992 | Stednitz et al. | 606/73 |
| 5,129,901 A | | 7/1992 | Decoste | 606/65 |
| 5,334,204 A | * | 8/1994 | Clewett et al. | 606/73 |
| 5,482,418 A | * | 1/1996 | Giannuzzi | 411/184 |
| 5,529,449 A | * | 6/1996 | McSherry et al. | 411/31 |
| 5,725,581 A | * | 3/1998 | Branemark | 623/16 |
| 5,860,973 A | | 1/1999 | Michelson | 606/61 |
| 5,968,098 A | * | 10/1999 | Winslow | 623/17 |
| 6,030,162 A | * | 2/2000 | Huebner | 411/413 |
| RE37,005 E | * | 12/2000 | Michelson et al. | 606/99 |
| 6,156,037 A | | 12/2000 | LeHuec et al. | 606/61 |
| 6,193,722 B1 | * | 2/2001 | Zech et al. | 606/79 |
| 6,224,596 B1 | * | 5/2001 | Jackson | 606/6 |
| 6,306,140 B1 | * | 10/2001 | Siddiqui | 606/73 |
| 6,508,818 B2 | * | 1/2003 | Steiner et al. | 606/69 |
| 2001/0007941 A1 | * | 7/2001 | Steiner et al. | 606/69 |

FOREIGN PATENT DOCUMENTS

| | | |
|---|---|---|
| DE | 867 422 | 1/1953 |
| DE | 297 10 979 | 8/1997 |
| EP | 0 809 975 | 12/1997 |
| GB | 231 155 | 7/1925 |
| GB | 2 294 399 | 5/1996 |
| WO | WO 96/08206 | 3/1996 |
| WO | WO 88/03781 | 6/1998 |

\* cited by examiner

*Primary Examiner*—Kevin Shaver
*Assistant Examiner*—Michael B. Priddy
(74) *Attorney, Agent, or Firm*—Pennie & Edmonds LLP

(57) ABSTRACT

A bone anchoring assembly includes at least one fixation plate and at least one bone anchoring element. Each bone anchoring element includes a circular-cylindrical hollow body with an upper end and a lower end, a connecting element that is pivotably mounted to a fixation plate or longitudinal support, an external thread that extends partially along the outer surface of the circular-cylindrical body for anchoring the bone anchoring element into the cortical portion of the bone, and a series of teeth located on the lower end of the circular-cylindrical body for cutting into bone.

50 Claims, 3 Drawing Sheets

SELF-CUTTING, HOLLOW-CYLINDRICAL BONE ANCHORING ASSEMBLY

CROSS REFERENCE TO RELATED APPLICATIONS

This application is a continuation of the U.S. National Stage designation of co-pending International Patent Application PCT/CH98/00359, filed Aug. 21, 1998, the entire content of which is expressly incorporated by reference.

FIELD OF THE INVENTION

The invention relates to a bone-anchoring assembly. More particularly, the invention relates to self-cutting, bone anchoring elements that are attachable to osteosynthesis fixation plates or longitudinal support bars for the fixation of bone segments, such as vertebra.

BACKGROUND OF THE INVENTION

Fixed implants such as bone plates, longitudinal support bars, pedicle screws, and bone anchoring assemblies increasingly are used in osteosynthesis applications. Such devices are useful for treating fractures of bones, for anchoring bone segments, or for providing support to bones weakened from disease or defect.

One such implant for the relative affixation of bone segments or vertebrae is disclosed in the German utility model DE 297 10 979 to Aesculap. The implant comprises a bone anchoring element that is insertable into a bone segment. The bone anchoring element can then be mounted using a detachable ball clamp to a connection element. The connection element can, in turn, be clamped to a longitudinal support or to another bone anchoring element. By connecting several bone anchoring elements together, bone segments or vertebra can be rigidly connected together. As disclosed in the German utility model, the anchoring elements are in the form of hollow, cylindrical bone screws that are externally threaded and fitted with radial boreholes located between the threads. The drawback, however, to this form of bone anchoring is that a seating duct must be drilled in the bone before the hollow, cylindrical anchoring elements can be inserted.

A similar shortcoming is present in the spinal interbody fusion assembly disclosed in U.S. Pat. No. 6,156,037 to LeHuec et. al. The spinal interbody fusion apparatus disclosed in this patent comprises an interbody fusion cage that has an external thread present along the entire length of the cage and a threaded stem located at the domed posterior end of the cage. A contoured plate threadably receives the cage stem and connects this cage to other interbody fusion cages. However, as mentioned earlier, the shortcoming to this apparatus is that a bone duct or bore must be drilled prior to the insertion of the interbody fusion cage.

A bone segment affixation implant comprising a hollow-cylindrical bone screw is disclosed in U.S. Pat. No. 5,015,247 to Michelson. This bone screw is designed for insertion in the intervertebral space and also consists of a hollow cylinder with an external thread and radial passages between the threads. Again, the drawback to this form of bone anchoring is that this implant must be inserted into a bone duct or bone borehole that has been previously drilled.

U.S. Pat. No. 4,537,185 to Stednitz also discloses a bone fixation screw with a hollow central cavity, a circular cylindrical anchoring section, a connecting element at the posterior end of the screw, and an external thread. In addition, this screw also has cutting teeth at the anterior end of the screw and the threads that are located on the external surface of the screw are self-cutting. The cutting teeth on the anterior portion of the screw and the external cutting threads allow the screw to be inserted into a bone segment without having to drill a bone duct or bone borehole. However, the drawback to using this bone anchoring is when the bone has been subject to osteoporosis or similar degenerative disease. Typically, the cortical region of the bone remains but the spongy portion of the bone is receded thus anchoring the screw into the spongy portion is not possible. Here, the circular cylindrical anchoring section of the bone screw is partially located in the spongy portion of the bone thus anchoring the bone screw in the bone is difficult. Also, the external thread of the bone screw extends into the anterior end of the screw which typically is located in the spongy portion of the bone. Having the thread extend into the spongy portion of the bone is disadvantageous because the micro-motion shear and notch effects that result from a self-cutting thread can harm the spongy region.

Another bone fixation screw having a hollow central cavity, a circular cylindrical anchoring section, a connecting element at the posterior end of the screw, anterior cutting teeth, and a self-cutting external thread is disclosed in U.S. Pat. No. 5,129,901 to Decoste. However, this bone fixation screw suffers from the same shortcoming as discussed above with the Stednitz bone screw.

In light of the foregoing, it is clear that there exists a need for an improved bone anchoring element.

SUMMARY OF THE INVENTION

The present invention relates to a bone anchoring assembly having at least one bone anchoring element capable of being attached to at least one osteosynthesis plate or bar for the fixation of bone segments. The at least one bone anchoring element preferably includes a circular-cylindrical hollow body fitted with cutting teeth at the anterior or lower end of the element, a connecting element at the posterior or upper end of the body for coupling to another fixation element, a plurality of radial borehole passages located on the body of the bone anchoring element, a flange located at the upper end of the body for limiting insertion depth of the bone anchoring element, and a self-tapping, external thread that extends over a portion of the bone anchoring element. Preferably, the connecting element is either circular-cylindrical or hexagonally-cylindrical in shape and houses a borehole that is configured and dimensioned to receive a fastener.

In one preferred embodiment, the bone anchoring element consists of a circular-cylindrical anchoring body fitted at one end with tangentially arranged cutting teeth. The number of cutting teeth range between 10 and 40, but preferably are between 25 and 35, with a clearance angle of any where from 5° to 40°, but preferably between 18° to 28°. The cutting edge of the teeth, typically, are at angle between 30° to 60° from the longitudinal axis of the bone anchoring body but preferably are at an angle between 40° and 50°, with the cutting corner of the teeth located at the outside surface of the anchoring body. Preferably, the rake of the cutting teeth is between 25° and 35°. At the other end of the anchoring body is a connecting element for coupling the anchoring body to another implantable element such as a fixation plate, an adjustment plate, or longitudinal supports. The connecting element is designed to couple with another implantable element in a pivoting fashion which allows the anchoring body to pivot with respect to the implantable element.

In another preferred embodiment, the outside surface of the anterior or lower portion of the anchoring element does not contain an external thread allowing for a smooth surface with radial borehole passages. The radial borehole passages allow the osteoinductive material located within the hollow anchoring body to fuse with the bone located outside the anchoring body. In addition, the radial borehole passages reduce the amount of material needed to create the implant, thereby substantially lowering the total weight of the bone anchoring element.

In a further preferred embodiment, the bone anchoring apparatus comprises at least two bone anchoring elements and at least one plate fitted with means to receive the connecting elements of the bone anchoring elements. The connecting element receiving means essentially consists of boreholes located in the plate appropriately sized to allow the connecting elements to be pivotably supported in the plate and detachably affixed to the plate by bone anchoring fasteners such as screws or nuts. Preferably, the connecting elements are pivotably connected to the plate so as to allow the bone anchoring elements to pivot between 60° and 120°. The connecting element receiving means are located throughout the plate in such a manner as to allow the at least two bone anchoring elements coupled to the plate to be displaced between 10 mm to 80 mm from each other along a single axis, but preferably be displaced between 20 mm to 60 mm from each other.

In another preferred embodiment, the bone anchoring apparatus further comprises at least two plates wherein each plate has an elongated central channel that extends along a central axis, across most of the length of the plate, capable of receiving a fastener that will affix the plates together at any distance along the central axis within the central channel. The fastener is preferably a screw or a bolt and the plates preferably have textured surfaces at their respective points of contact to prevent slippage of the plates with respect to each other and to increase the stability of the affixed plates. In addition, the plates preferably have lateral lugs to further prevent slippage and to prevent rotation of the plates with respect to each other.

In a further preferred embodiment, the bone anchoring apparatus further comprises two annular disks and at least one plate, wherein one disk is fixably mounted to the plate and the second disk is mounted within the elongated channel of the plate to allow variable spacing between the two disks. Each disk receives the connecting element of the bone anchoring element to pivotably couple the bone anchoring element to the plate through the disk.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
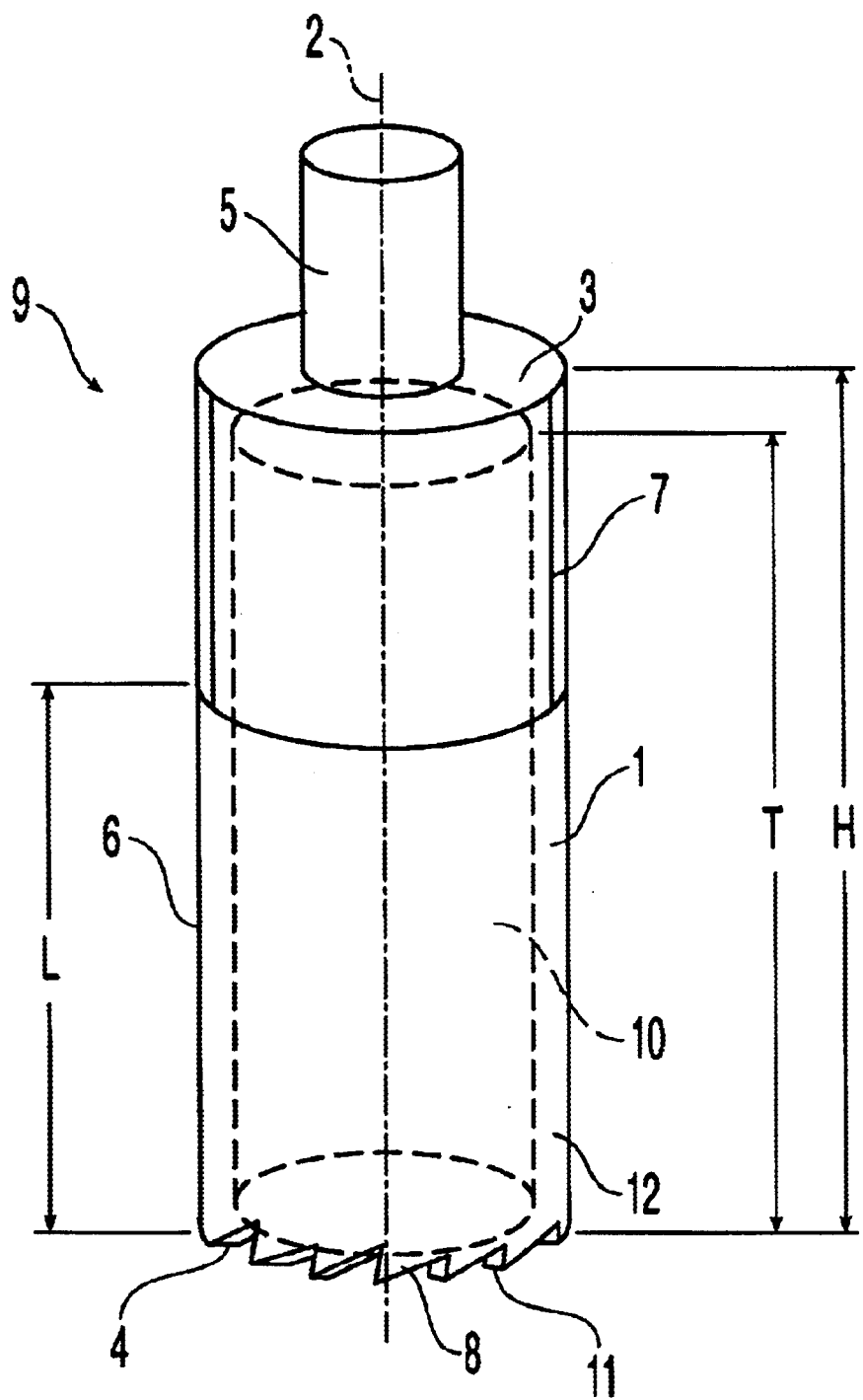
FIG. 1 shows a schematic view of a bone anchoring element of the present invention.

Referring to FIG. 1, bone anchoring element 12 of bone anchoring assembly 9 is shown schematically. In a preferred embodiment, bone anchoring element 12 comprises circular-cylindrical body 1, connecting element 5, and cutting teeth 8. Connecting element 5 is attached directly to circular-cylindrical body 1 at upper end 3 and is located coaxially to longitudinal axis 2 of circular-cylindrical body 1. In addition, connecting element 5 is also, preferably, circularly-cylindrical or hexagonally-cylindrical in shape. Cutting teeth 8 are located tangentially to lower surface 4 of circular-cylindrical body 1 and the cutting surfaces of cutting teeth 8 run radially inward from the outer circumference of circular-cylindrical body 1 as evidenced by radial cutting edge 11. Circular-cylindrical body 1 has a certain height, designated as H. Circular-cylindrical body 1 also has concentric borehole 10 which, measured from lower surface 4, has a depth of T. Thus, circular-cylindrical body 1 is hollow over a length corresponding to the depth of T. Outer surface 6 of circular-cylindrical body 1 is smooth over the anterior or lower portion of circular-cylindrical body 1 and is marked as L. The remaining portion of outer surface 6 contains external thread 7 and, accordingly, is not smooth.

Figure 2:
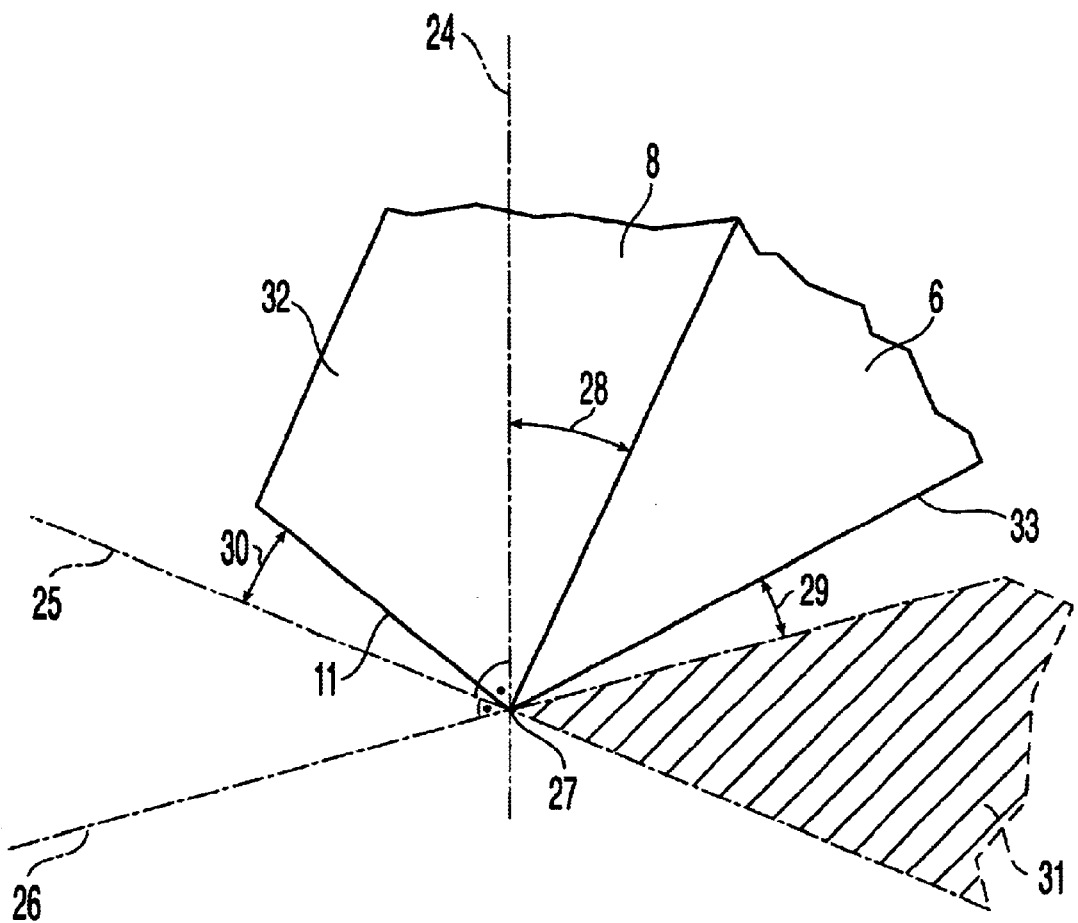
FIG. 2 shows a detailed view of a cutting tooth of the bone anchoring element of FIG. 1.

FIG. 2 shows a detailed view of a single tooth 32 taken from cutting teeth 8. Defined in the figure, for ease of explanation, is a coordinate axis wherein the z-axis is parallel to longitudinal axis 24, the radial x-axis is parallel to axis 25, and the y-axis is parallel to axis 26. Located at the outer edge of the end of tooth 32 is cutting tip 27. Cutting tip angle 28, which preferably is 30°, is the angle of cutting tip 27 from the plane formed by axis 24 and axis 25. This angle represents the angle of the surface from the plane perpendicular to the cutting surface that the bone chips run on after being cut by radial cutting edge 11. Clearance angle 29, which preferably is 22.5°, represents the angle of outer cutting edge 33 from plane 31, which is formed by axis 25 and axis 26. Finally, bias angle 30, which preferably is 45°, represents the angle between radial cutting edge 11 and plane 31, which is formed by axis 25 and axis 26. The bias angle of radial cutting edge 11 allows the bone chips generated from the cutting teeth to be guided inwards toward borehole 10 of circular-cylindrical body 1.

Figure 3:
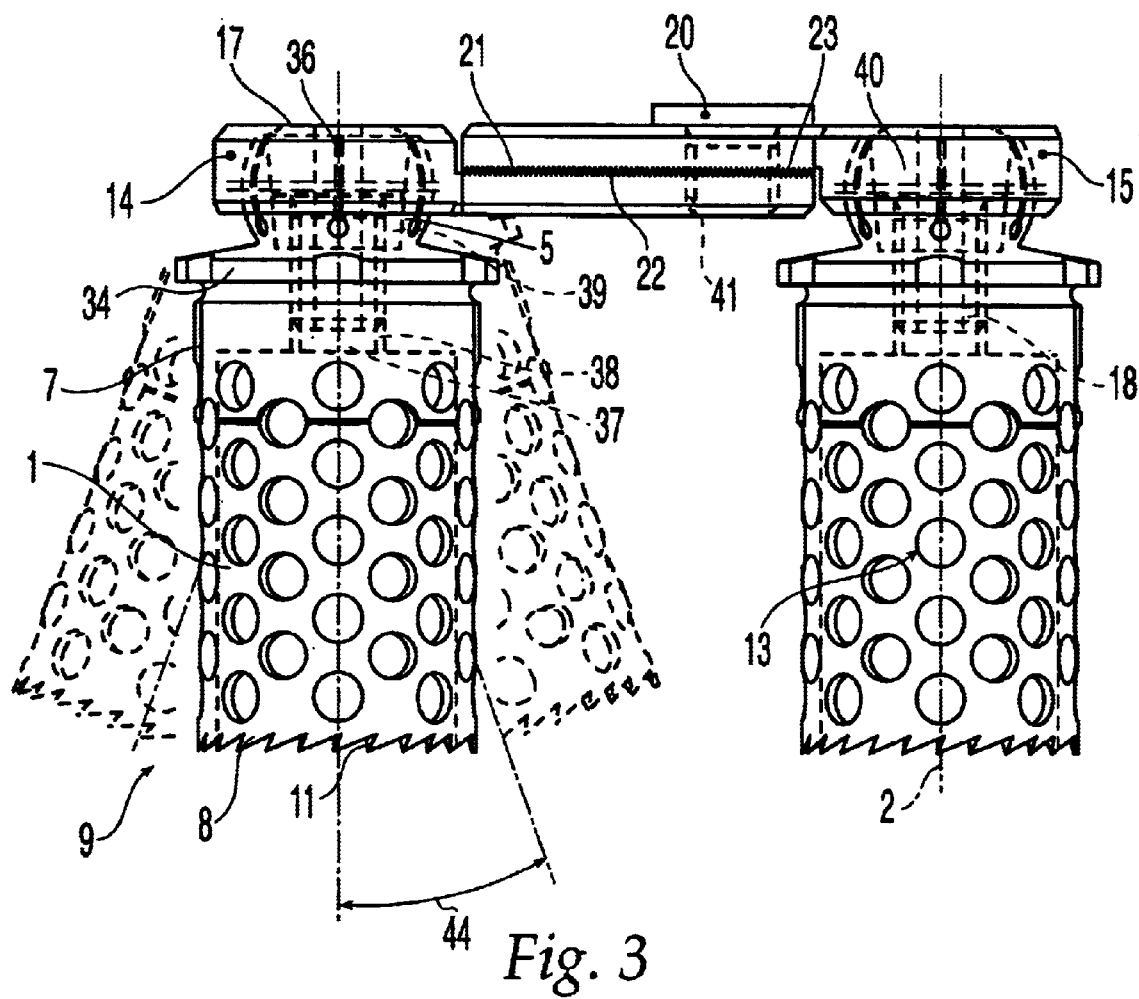
FIG. 3 shows a perspective view of a bone anchoring assembly of the present invention.
Figure 4:
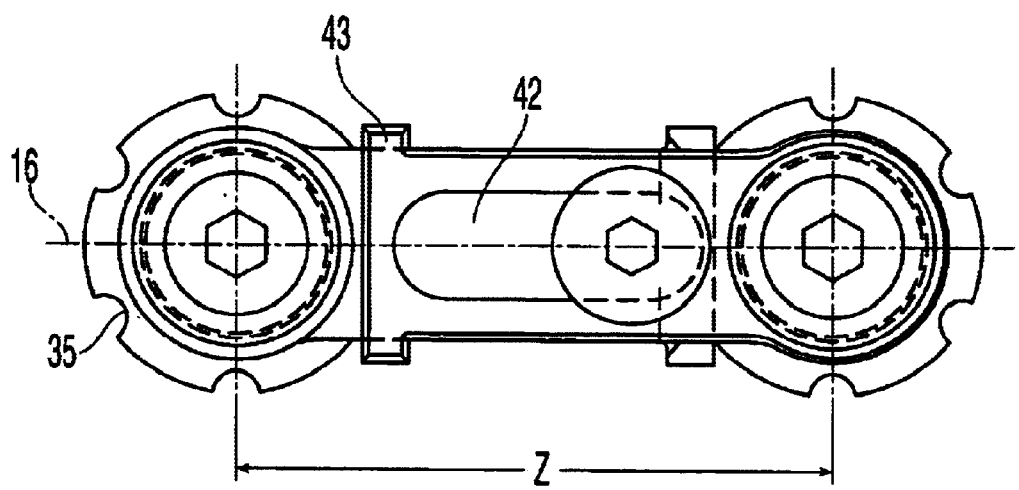
FIG. 4 shows a top view of the bone anchoring assembly of FIG. 3.

Turning now to FIGS. 3 and 4, another preferred embodiment of bone anchoring assembly 9 is shown. In this embodiment, bone anchoring assembly 9 comprises two bone anchoring elements, shown as circular-cylindrical bodies 1, and two fixation plates 14, 15. Defined centrally along the length of fixation plates 14, 15 is central axis 16. Fixation plate 14 has contacting surface 21 that is placed in contact with contacting surface 22 of fixation plate 15 when the two fixation plates are coupled together via elongated slots 42 and fastener 20. The contacting surfaces 21, 22 are textured, typically in the form of serrations 23, to help prevent fixation plates 14, 15 from slipping when a load is placed on fixation plates 14, 15. In addition, fixation plates 14, 15 both have lateral lugs 43 which are located at the ends of contacting surfaces 21, 22. Lateral lugs 43 prevent fixation plates 14, 15 from rotating relative to each other thereby becoming skewed with respect to central axis 16.

Circular-cylindrical bodies 1 have a plurality of radial borehole passages 13 located along the outside surface of circular-cylindrical bodies 1, have external threads 7 located at the posterior or upper ends of circular-cylindrical bodies 1, and have cutting teeth 8 with radial cutting edges 11 located at the anterior or lower end of the bodies. Radial borehole passages 13 provide a passageway to allow the osteoinductive material located within the borehole of circular-cylindrical bodies 1 to communicate with the bony tissue located outside of circular-cylindrical bodies 1. External threads 7 anchor circular-cylindrical bodies 1 to the bony tissue. Circular-cylindrical bodies 1 also have flange 34 located at the posterior or upper end of the bodies. Flange 34, preferably, has six semi-circular notches 35 located equidistantly along the periphery of the flange. Through the use of notches 35 and a matching tool, circular-cylindrical body 1 can be rotated into bone. Alternatively, flange 34 can be in the shape of a hexagon and a hexagonal tool can be used to rotate circular-cylindrical body 1 into bone. Further, flange 34 also acts as a stop to prevent circular-cylindrical bodies 1 from being rotated excessively deep into the bone. Circular-cylindrical bodies 1 also have connecting elements 5 which are used to couple circular-cylindrical bodies 1 to fixation plates 14, 15. Connecting elements 5 are spherical in shape with diameters that correspond to the size of the receiving boreholes 17 located in fixation plates 14, 15. Also, both connecting elements 5 are fitted with boreholes 37 that have internal thread 38, a conically lathed geometry 39, and a series of slits 36 located along the periphery of connecting elements 5. Screws 18 are inserted into boreholes 37 through receiving boreholes 17 wherein screw heads 40 fit within the conically lathed geometry 39 to fix circular-cylindrical bodies 1 to fixation plates 14,15. More specifically, when screws 18 are tightened, the walls of connecting elements 5 are clamped against the walls of receiving boreholes 17 thereby affixing circular-cylindrical bodies 1 to fixation plates 14, 15.

The structure and means for affixing the circular-cylindrical bodies 1 to fixation plates 14, 15 and for coupling fixation plates 14, 15 together allow circular-cylindrical bodies 1 to be attached at various angles and distances from each other. For example, the spherical structure of connecting elements 5 allow circular-cylindrical bodies 1 to be attached to fixation plates 14, 15 at angle 44 which ranges from 16° inwardly from perpendicular axis 2 to 19° outwardly from perpendicular axis 2. In addition, fastener 20, which typically is in the form of a screw, is threadably received in borehole 41 which can be located any where within elongated slot 42. By using elongated slot 42 with borehole 41, fixation plates 14, 15 can be coupled together at various displacement distances Z, thereby varying the distance between circular-cylindrical bodies 1.

As mentioned earlier, the insertion of the above described bone anchoring assembly does not require a previously drilled borehole or duct. The procedure for inserting and locking the bone anchoring assembly into a bone is very quick and quite simple. The first step in inserting the assembly into bone is to introduce a Kirschner wire into the bone. The Kirschner wire is used to guide circular-cylindrical bodies 1 as they are inserted into the bone. A first circular cylindrical body 1 is then rotated into the bone using flange 34 and a matching tool. As circular-cylindrical body 1 is rotated into the bone, cutting teeth 8 with radial cutting edges 11 cut the bone creating bone chips which are guided into borehole 10 located within circular-cylindrical body 1. External thread 7 anchors circular-cylindrical body 1 in the bone. Since external thread 7 is present only on the upper portion of circular-cylindrical body 1, circular-cylindrical body 1 is anchored only to the cortical portion of the bone and not to the spongy portion of the bone. Furthermore, since external thread 7 does not enter into the spongy portion of the bone, external thread 7 will not harm the spongy portion of the bone through micro-motion shears and notch effects. After first circular-cylindrical body 1 has been screwed into the bone, the Kirschner wire may then be removed. A second circular-cylindrical body 1 is then inserted into the bone in the same manner as first circular-cylindrical body 1. After circular-cylindrical bodies 1 have been inserted into the bone, fixation plates 14, 15 are attached to circular-cylindrical bodies 1 by inserting screws 18 through boreholes 37 located in connecting elements 5 and receiving boreholes 17 located in fixation plates 14, 15. Fastener 20 is then threadably received through borehole 41 thereby coupling fixation plates 14, 15 together. Finally, the bone anchoring assembly, as a whole, can then be locked in the desired position by tightening screws 18 and fastener 20.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A bone anchoring element comprising:
   a hollow cylindrical body with a threaded upper end, a smooth lower end, and a plurality of boreholes extending into the body between the upper and lower ends;
   a connecting element disposed proximate the upper end for coupling to a fixation device; and
   at least one tooth extending from the lower end for cutting into bony tissue.

2. The bone anchoring element of claim 1, further comprising a fixation device wherein the fixation device is a plate.

3. A bone anchoring element comprising:
   a hollow cylindrical body with an upper end and a lower end;
   a connecting element at the upper end of the body for coupling to a fixation device;
   at least one tooth extending from the lower end of the body for cutting into bony tissue;
   threading on an exterior surface of the body for anchoring the body into surrounding bony tissue,
   wherein the threading is near the upper end of the body and the lower end of the body is smooth, and the connecting element pivotably couples to the fixation device.

4. The bone anchoring element of claim 3, further comprising a plurality of radial boreholes extending through the hollow cylindrical body between the upper and lower ends.

5. The bone anchoring element of claim 3, wherein the at least one tooth extends tangentially from the lower end of the body.

6. The bone anchoring element of claim 5, wherein the at least one tooth has radial cutting edges that form an angle between 30° and 60° from a plane determined by a radial axis of the body and an associated tangential axis.

7. The bone anchoring element of claim 6, wherein the at least one tooth has edges that extend along a back of each tooth from the radial cutting edge to the lower end of the body and each of the edges forms an angle between 15° and 30° from the plane determined by the radial axis of the body and the associated tangential axis.

8. The bone anchoring element of claim 6, wherein the at least one tooth has a rake between 25° and 35°.

9. The bone anchoring element of claim 3, wherein the connecting element is circular-cylindrical or hexagonal-cylindrical.

10. The bone anchoring element of claim 3, wherein the connecting element concentrically houses a borehole configured and dimensioned to receive a fastener.

11. The bone anchoring element of claim 3, further comprising a flange located at the upper end of the body for limiting the insertion depth of the bone anchoring element.

12. The bone anchoring element of claim 11, wherein the flange has a plurality of notches for receiving an insertion tool.

13. The bone anchoring element of claim 11, wherein the flange is hexagonal.

14. A bone anchoring element comprising:
   a hollow cylindrical body with an upper end and a lower end;
   a flange located at the upper end of the body for limiting the insertion depth of the bone anchoring element;
   a connecting element located above the flange at the upper end of the body for coupling to a fixation device; and
   at least one tooth extending from the lower end of the body for cutting into bony tissue.

15. The bone anchoring element of claim 14, wherein the flange has a plurality of notches for receiving an insertion tool.

16. The bone anchoring element of claim 14, wherein the flange is hexagonal.

17. The bone anchoring element of claim 14, wherein the connecting element pivotably couples to a fixation device.

18. The bone anchoring element of claim 14, further comprising a plurality of radial boreholes in an exterior surface of the hollow cylindrical body.

19. A bone anchoring assembly comprising:
   a first fixation plate having a first end, a second end, and a central axis; and
   a first bone anchoring element having a hollow cylindrical body with an upper end and a lower end, a connecting element at the upper end for coupling to the first fixation plate, and at least one tooth extending from the lower end for cutting into bony tissue;
   wherein the first fixation plate further comprises an elongated slot located along the central axis at the first end and a borehole configured and dimensioned to pivotably receive the connecting element of the first bone anchoring element and located at the second end.

20. The bone anchoring assembly of claim 19, further comprising:
   a second bone anchoring element,
   wherein the elongated slot is configured and dimensioned to pivotably receive the connecting element of the first bone anchoring element thereby allowing relative displacement between the first bone anchoring element when pivotably coupled to the elongated slot and the second bone anchoring element when pivotably coupled to the borehole.

21. The bone anchoring assembly of claim 19, further comprising:
   a second fixation plate having a first end, a second end, and an elongated slot; and
   a second bone anchoring element having a hollow cylindrical body with an upper end and a lower end, and having a connecting element at the upper end for coupling to the second fixation plate;
   wherein the elongated slots of the first and second fixation plates are configured and dimensioned to receive a fastener thereby allowing the fixation plates to be coupled together at varying separation distances along the central axis; and the connecting elements of the bone anchoring elements have boreholes configured and dimensioned to receive fasteners allowing the bone anchoring elements to be pivotably coupled to the fixation plates.

22. The bone anchoring apparatus of claim 21, wherein the separation distance between the bone anchoring elements can be varied between 20 mm and 60 mm.

23. The bone anchoring apparatus of claim 21, wherein the first end of each fixation plate is textured.

24. The bone anchoring apparatus of claim 21, wherein the fixation plates have lateral extensions at the first end of each fixation plate for limiting the rotation of the fixation plates with respect to the central axis.

25. A bone anchoring assembly comprising:
   a hollow cylindrical body with an upper end and a lower end;
   a connecting element at the upper end of the body for coupling to a fixation device;
   at least one tooth extending from the lower end of the body for cutting into bony tissue; and
   a fixation rod having a first end, a second end, and an axis extending along the longitudinal length of the rod,
   wherein at least one borehole configured and dimensioned to pivotably receive the connecting element is located along the axis between the first and second ends of the fixation rod.

26. A bone anchoring element comprising:
   a hollow cylindrical body with an upper end a lower end;
   a connecting element at the upper end of the body for coupling to a fixation device;
   at least one tooth extending from the lower end of the body for cutting into bony tissue,
   wherein the at least one tooth extends tangentially from the lower end of the body and has radial cutting edges that form an angle between 30° and 60° from a plane determined by a radial axis and an associated tangential axis.

27. The bone anchoring element of claim 26, wherein the body has at least two teeth and the teeth have edges that extend along a back of each tooth from the radial cutting edge to the lower end of the body and each of the edges forms an angle between 15° and 30° from a plane determined by the radial axis of the body and the associated tangential axis.

28. The bone anchoring element of claim 27, wherein the teeth have a rake between 25° and 35°.

29. The bone anchoring element of claim 26, further comprising a plurality of radial boreholes extending through the hollow cylindrical body between the upper and lower ends.

30. The bone anchoring element of claim 29, further comprising a threading on an exterior surface of the body for anchoring the body into bony tissue, wherein the threading is near the upper end of the body and the lower end of the body is smooth.

31. The bone anchoring element of claim 26, further comprising a threading on an exterior surface of the body for anchoring the body into surrounding bony tissue.

32. The bone anchoring element of claim 31, wherein the threading is self-tapping.

33. The bone anchoring element of claim 31, wherein the threading is near the upper end of the body and the lower end of the body is smooth.

34. A bone anchoring element comprising:
   a hollow cylindrical body with an upper end and a lower end;
   a connecting element at the upper end of the body for coupling to a fixation device;
   a flange located at the upper end of the body for limiting the insertion depth of the bone anchoring element; and
   at least one tooth extending from the lower end of the body for cutting into bony tissue,
   wherein the flange has a plurality of notches for receiving an insertion tool.

35. The bone anchoring element of claim 34, wherein the connecting element concentrically houses a borehole configured and dimensioned to receive a fastener.

36. A bone anchoring element comprising:
   a hollow cylindrical body with an upper end and a lower end;
   a connecting element at the upper end of the body for coupling to a fixation device;
   at least one tooth extending from the lower end of the body for cutting into bony tissue;
   a plurality of radial boreholes in an exterior surface of the body; and
   threading on the exterior surface of the body for anchoring the body into surrounding bony tissue, wherein the threading is near the upper end of the body and the lower end of the body is smooth.

37. A bone anchoring element comprising:
a hollow cylindrical body with an upper end and a lower end;
a connecting element at the upper end of the body for coupling to a fixation device;
at least one tooth extending from the lower end of the body for cutting into bony tissue; and
a flange located at the upper end of the body for limiting the insertion depth of the bone anchoring element,
wherein the flange has a plurality of notches for receiving an insertion tool.

38. A bone anchoring element comprising:
a hollow cylindrical body with an upper end and a lower end;
a flange disposed proximate the upper end;
a connecting element disposed proximate the upper end and configured and dimensioned for pivotable coupling fixation device; and
at least one tooth extending from the lower end of the body for cutting into bony tissue.

39. The bone anchoring element of claim 38, further comprising a fixation device wherein the fixation device is a plate.

40. A bone anchoring element comprising:
a hollow cylindrical body with an upper end and a lower end;
a flange disposed proximate the upper end and comprising a plurality of notches for receiving an insertion tool;
a connecting element disposed proximate the upper end for coupling to a fixation device; and
at least one tooth extending from the lower end of the body for cutting into bony tissue.

41. The bone anchoring element of claim 41, further comprising a fixation device wherein the fixation device is a plate.

42. A bone anchoring assembly comprising:
a first cylindrical body pivotably connected to a first plate;
a second cylindrical body pivotably connected to a second plate; and
teeth disposed on a free end of each of the first and second cylindrical bodies;
wherein the first and second plates are configured and dimensioned to be coupled together to permit the distance between the cylindrical bodies to be adjusted.

43. The bone anchoring assembly of claim 42, wherein the first cylindrical body further comprises threading.

44. The bone anchoring assembly of claim 43, wherein the second cylindrical body further comprises threading.

45. The bone anchoring assembly of claim 44, wherein the first cylindrical body further comprises a flanged disposed proximate an upper end thereof.

46. The bone anchoring assembly of claim 42, wherein the first plate comprises a slot, and the plates are coupled together by a fastener extending through the slot.

47. The bone anchoring assembly of claim 42, wherein the first and second plates each comprise a textured surface, and the textured surfaces contact each other.

48. The bone anchoring assembly of claim 42, wherein the first cylindrical body is pivotably connected to the first plate with an expandable connector.

49. The bone anchoring assembly of claim 48, wherein the expandable connector comprises a connector body with an arcuate outer surface and a borehole.

50. The bone anchoring assembly of claim 49, further comprising a screw threadably received in the borehole of the connector body.

* * * * *